United States Patent [19]

Lepp et al.

[11] Patent Number: 4,707,237
[45] Date of Patent: Nov. 17, 1987

[54] SYSTEM FOR IDENTIFICATION OF CELLS BY ELECTROPHORESIS

[75] Inventors: Cyrus A. Lepp, Stoughton, Mass.; James J. Mussatto, Fairfax Station, Va.; James M. Ziegenmeyer, Lexington, Mass.

[73] Assignee: Ciba Corning Diagnostics Corp., Medford, Mass.

[21] Appl. No.: 416,461

[22] Filed: Sep. 9, 1982

[51] Int. Cl.[4] .......................................... G01N 27/26
[52] U.S. Cl. .............................. 204/182.8; 204/299 R
[58] Field of Search ............. 204/180 G, 299 R, 182.8

[56] References Cited

U.S. PATENT DOCUMENTS

| | | | |
|---|---|---|---|
| 3,936,356 | 2/1976 | Janin | 195/103.5 R |
| 3,992,265 | 11/1976 | Hansen | 195/127 |
| 4,018,662 | 4/1977 | Ruhenstroth-Bauer et al. | 204/180 G |
| 4,024,530 | 5/1977 | Hughes | 340/332 |
| 4,056,359 | 3/1977 | Janin | 23/259 |
| 4,129,483 | 12/1978 | Bochner | 195/100 |
| 4,391,688 | 7/1983 | Hamelin | 204/180 G |
| 4,415,418 | 11/1983 | Turre et al. | 204/180 G |
| 4,420,383 | 12/1983 | Fujiwara et al. | 204/180 G |

FOREIGN PATENT DOCUMENTS

| | | |
|---|---|---|
| 0070153 | 1/1983 | European Pat. Off. . |
| 0076123 | 4/1983 | European Pat. Off. . |
| 1596811 | 3/1981 | United Kingdom . |
| 1596812 | 3/1981 | United Kingdom . |

OTHER PUBLICATIONS

Heftmann, Erich, *Chromatography*, Reinhold Publishing Corporation, New York, pp. 260–262, (1967).

McDonald, Hugh J., *Ionography; Electrophoresis in Stabilized Media*, The Year Book Publishers, Inc., pp. 112–113, (1955).

R. D. Strickland, *Anal. Chem.*, 42, 32R (1970).

Broad, William J., *Science*, vol. 210, Dec. 12, 1980, pp. 1229–1230.

Dickson, David, *Nature*, vol. 289, Jan. 22, 1981, p. 227.

Gartler, S., *Nature*, vol. 217, 1968, pp. 750–751.

Harris, N. L., Gang, D. L., Quay, S. C., Poppema, S., Zamecnik, P. C., Nelson-Rees, W. A., O'Brien, S. J., *Nature*, vol. 289, Jan. 22, 1981, pp. 228–230.

Michl, Heribert, "Techniques of Electrophoresis", *Chromatogrpahy*, pp. 282–311.

Nelson-Rees, W. A., Daniels, D. W., Flandermeyer, R. R., *Science*, vol. 212, Apr. 24, 1981, pp. 446–452.

O'Brien, S. J., Shannon, J. E., Gail, M. H., *In Vitro*, vol. 16, No. 2, 1981, pp. 119–135.

O'Brien, S. J., Simonson, J. M., Grabowski, M. W., Barile, M. F., *Journal of Bacteriology*, Apr. 1981, pp. 222–232.

Peterson, W. D. Jr., Simpson, W. F., Hukku, B., *Methods in Enzymology*, vol. LVIII, 1979, pp. 164–178.

Stulberg, C. S., Peterson, W. D. Jr., Simpson, W. F., *American Journal of Hematology*, vol. 1, 1976, pp. 237–242.

Wieme, R. J., "Theory of Electrophoresis", *Chromatography*, pp. 228–281.

*Primary Examiner*—John F. Niebling
*Attorney, Agent, or Firm*—D. Reitenbach

[57] ABSTRACT

Cells are identified electrophoretically through isoenzyme analysis. The use of standard and control cells allows semi-skilled workers to achieve reproducible results. A coding sequence is assigned to the cels to be identified using a grid to interpret the electrophoretic separations observed on a series of electrophoretic films, each film being developed for a particular isoenzyme. Comparison of the coding sequence with a compendium of coding sequences for known cells identifies the cells to be identified.

38 Claims, 11 Drawing Figures

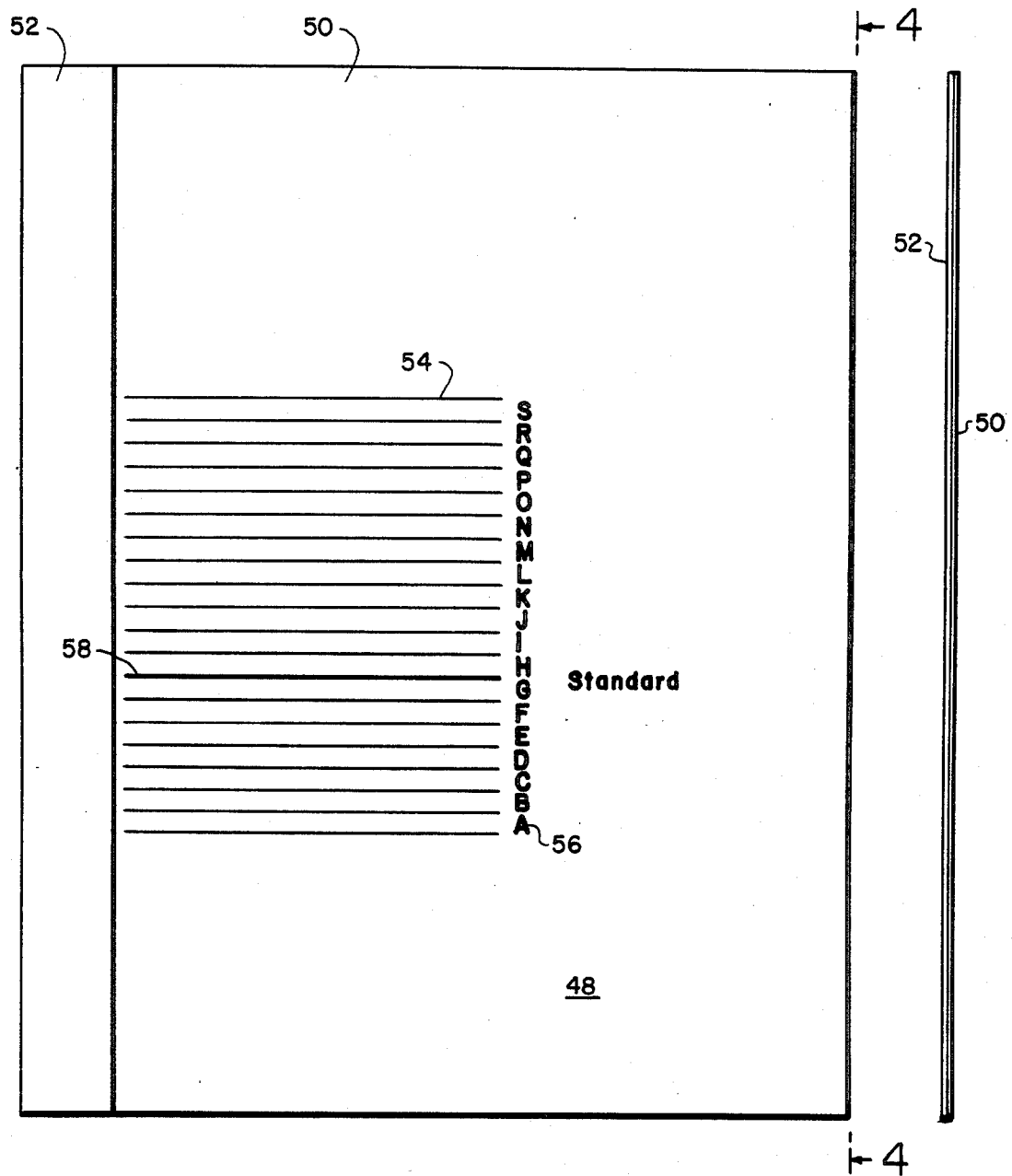

| FHAOLNG OEHMJBR | | | | | | | Cell Line |
|---|---|---|---|---|---|---|---|
| [1]NP | [2]G6PD | [3]MD | [4]MPI | [5]PepB | [6]AST | [7]LD | |
| F | H | A | O | L | N | G | Pig |
| F | I | I | J | K | U | G | Dog |
| F | I | I | L | K | M | G | Green Monkey |
| G | H | I | K | K | U | H | Mink |
| G | K | S | I | M | L | O | Rat |
| H | H-I | K | I | I | O | O | Human |
| K | D | J | J | K | J | M | Buffalo |
| K | I | I | L | K | M | G | Rhesus Monkey |
| K | J | J | J | K | O | K | Syrian Hamster |
| K | J | H | K | K | N | J | Chinese Hamster |
| M | I | I | N | M | N | K | Rabbit |
| O | E | H | M | J | B | R | Frog |

FIG.7

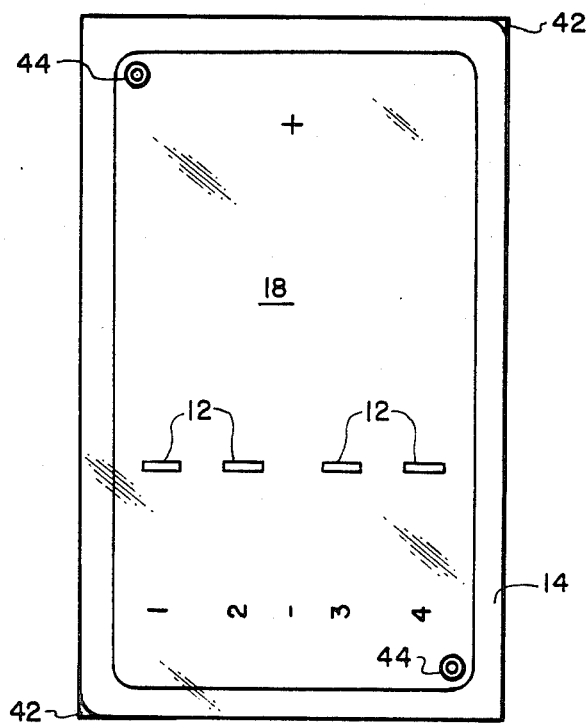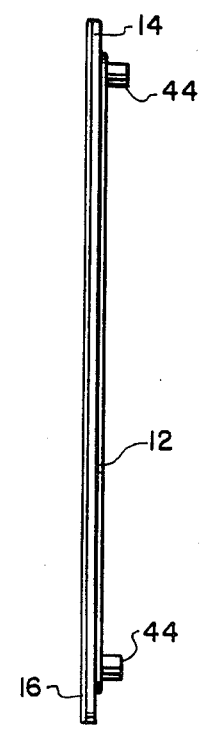
FIG.8   FIG.9
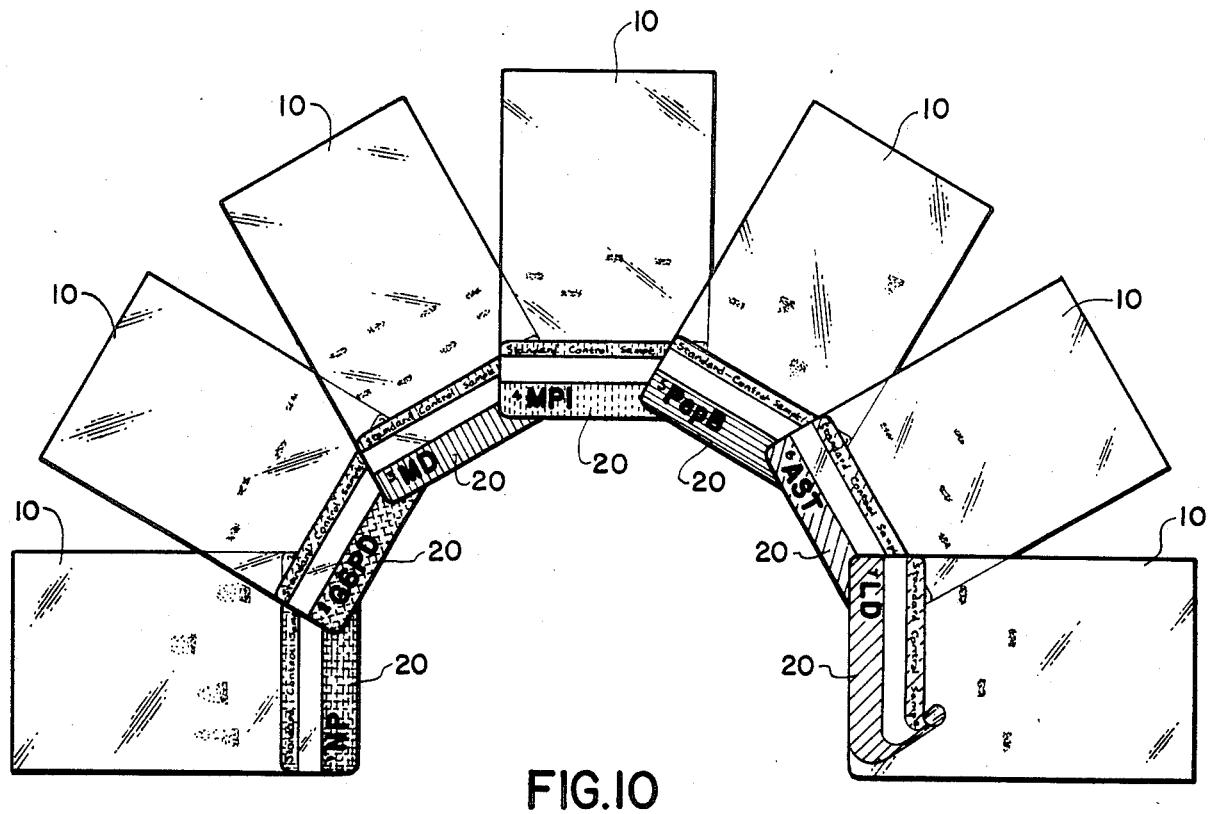
FIG.10

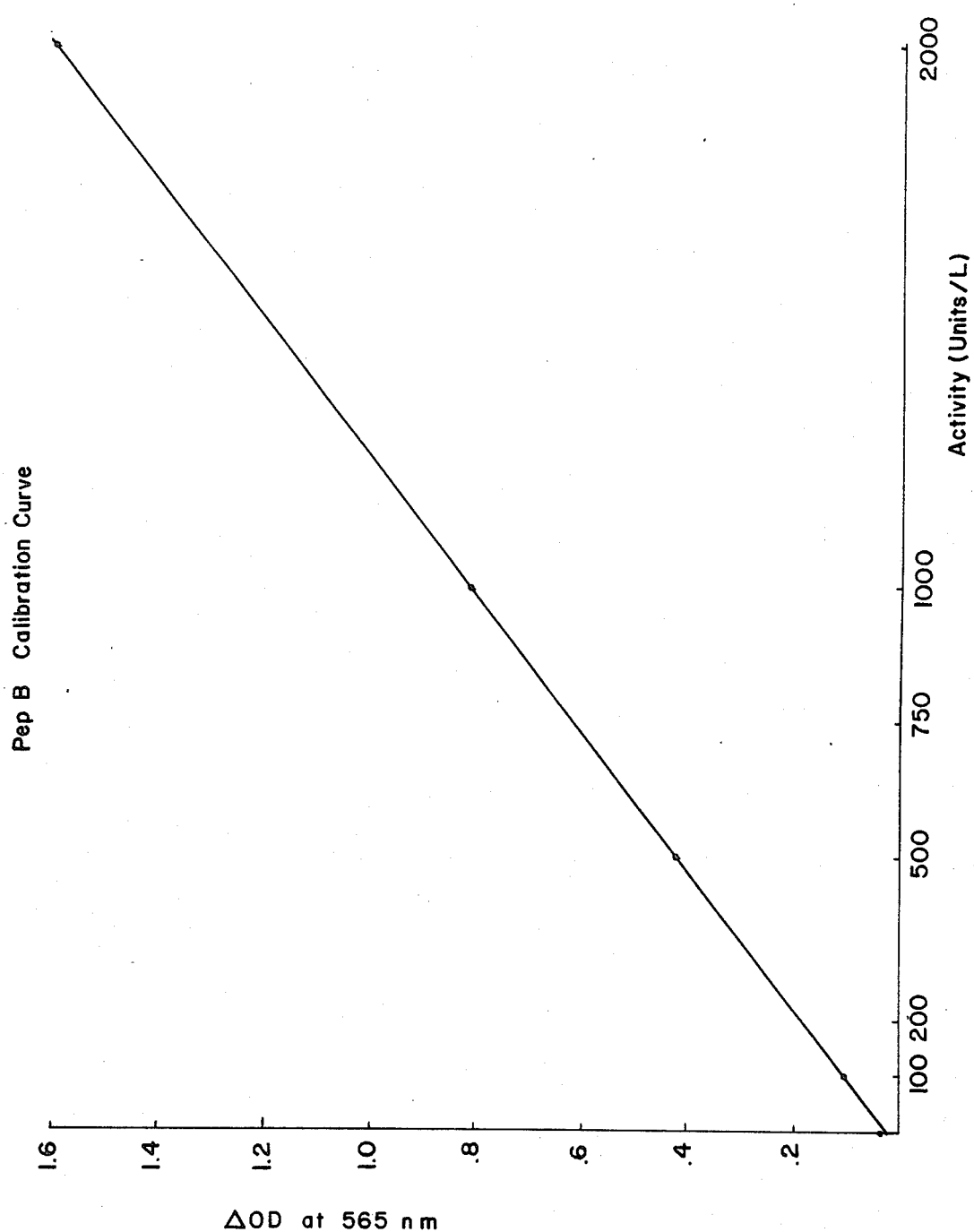

SYSTEM FOR IDENTIFICATION OF CELLS BY ELECTROPHORESIS

BACKGROUND OF THE INVENTION

1. Field of the Invention

This invention relates to the identification of cells by electrophoresis. More particularly, the invention relates to a system for cell identification which can be easily used by semi-skilled workers and yet produce consistently reproducible results.

2. Description of the Prior Art

The identification of biological cells has been a long standing problem in the biological sciences. A variety of techniques have been applied to the problem. For example, infectious microorganisms have been identified in clinical laboratories by means of simultaneously applied biochemical reactions. Vertebrate, plant and mycoplasma cells have been characterized in some research laboratories by specilized techniques including sophisticated isoenzyme electrophoresis, cell surface antigen analysis and chromosome analysis.

The problem of identifying cells is particularly acute when cells are grown in tissue culture. Because the tissue culture medium is designed to encourage cell growth, it is highly susceptible to contamination. As a result, a tissue culture thought to be growing a particular type of cell, in fact, through contamination, can be growing either a combination of the original cells and the contaminating cells, or, depending on the relative viability of the original cells and the contaminating cells, just the contaminating cells. Accordingly, when a researcher conducts experiments and reaches conclusions based on tissue culture work, and couples those results and conclusions to a particular type of cell, he may be misleading both himself and the public with regard to his work. Numerous examples of such contamination have been documented in the biological literature. Indeed, in 1976, it was reported in the *American Journal of Hematology* that approximately 30% of a series of tissue culture cells studied were incorrectly designated by the submitting investigator. See C. S. Stulberg, W. D. Peterson, Jr., and W. F. Simpson, "Identification of Cells in Culture", *American Journal of Hematology*, Volume 1, pages 237-242 (1976).

The problem of contamination of tissue culture cells was identified at least as early as the late 1960's. See, for example, S. Gartler "Apparent HeLa Cell Contamination of Human Heteroploid Lines," *Nature,* Volume 217, pages 750-751 (1968). Yet, reports of contaminated tissue culture cells continue to appear in the literature. See, for example, D. Dickson, "Contaminated Cell Lines", *Nature,* Volume 289, page 227 (1981).

Of significance with regard to each of these reports of contaminated tissue culture cells is the fact that the contamination was found only by means of highly sophisticated and time consuming procedures using expensive equipment in the hands of experts in the area of cell identification. Moreover, none of the procedures used by these experts included provisions for standardization of the system or provisions for the inclusion of a control to verify the performance of the system. Also, in order to confirm any cell identification, these investigators maintained large stocks of reference cells. For all of these reasons, the procedures previously used for identification of cells have not been reproducible enough in various investigators' hands to be of general utility.

SUMMARY OF THE INVENTION

It is an object of this invention to provide a system for the identification of cells which overcomes the problems inherent in the prior art systems. In particular, it is an object of the invention to provide a cell identification system which can be used generally in various laboratories and which will produce reproducible results within any one laboratory and among various laboratories. Moreover, it is an object of the invention to provide a cell identification system which is easy to use by semi-skilled workers. It is a further object of the invention to provide a cell identification system which is inexpensive to use.

In accordance with one aspect of the invention, an electrophoretic method for identifying cells is provided which includes:

performing an electrophoretic separation on a sample from each of a first, a second and a third population of cells, the first population being of the cells to be identified and the second and third populations being of cells whose identities are known, each of the samples containing at least some electrophoretically separable substances which are characteristic of known cells, the separations being performed under comparable conditions;

developing the electrophoretic separations with regard to one or more electrophoretically separable substances which are characteristic of known cells, the substances chosen for development being known to be produced by cells of both the second and third populations and the number of substances chosen for development being sufficient to characterize the cells to be identified;

comparing the developed separations for the second and third samples to determine the range of separation for the chosen substances under the conditions used; and based on the range of separation so determined, comparing the separations for the first and second samples to determine the identity of the cells of the first population.

In accordance with another aspect of the invention, a method for identifying cells is provided which includes:

preparing an extract from a population of the cells to be identified, the extract containing substances which are produced by the cells and which are electrophoretically separable;

performing electrophoretic separations on a series of samples from the extract;

developing the electrophoretically separated samples with regard to a series of preselected substances known to be electrophoretically separable and known to be produced by at least some cells, each sample being developed for one such substance and the number of substances in the series being sufficient to characterize the cells to be identified;

determining from the developed samples the electrophoretic mobility exhibited by the cells to be identified for each of the preselected substances;

assigning to the electrophoretic mobility for each substance so determined a symbolic representation;

arranging the symbolic representations in a predetermined order to form a coding sequence; and comparing the coding sequence with a compendium of coding sequences for known cells to determine the identity of the cells to be identified.

In accordance with a further aspect of the invention, a method for electrophoretically identifying cells is provided which includes:

selecting a series of electrophoretically separable substances, the number of substances in the series being sufficient to permit characterization of the cells to be identified;

performing a first set of electrophoretic separations on extracts from a plurality of known cells, the separations being performed under conditions which limit the differences in distances migrated for the series of substances and for the plurality of known cells to a defined range corresponding to a predetermined scale for interpreting the separations;

developing the first set of separations for the series of electrophoretically separable substances;

interpreting the first set of developed separations using the predetermined scale so as to assign a sequencing code to each of the known cells;

performing a second set of electrophoretic separations on extracts from the cells to be identified under the conditions used for the known cells;

developing the second set of separations for the series of electrophoretically separable substances;

interpreting the second set of developed separations using the predetermined scale so as to assign a sequencing code to the cells to be identified; and comparing the sequencing code for the cells to be identified with the sequencing codes for the known cells to determine the identity of the cells to be identified.

In accordance with a still further aspect of the invention, a method for identifying cells is provided which includes:

electrophoretically separating extracts from standard cells, control cells and the cells to be identified on separate tracks of an electrophoretic film;

developing the electrophoretic film with regard to a first preselected electrophoretically separable substance using a reagent specific for that substance to produce a pattern of one or more bands of an insoluble product in each track for which the substance is present in the extract, the pattern, where present, being indicative of the extent of electrophoretic migration of the first preselected substance for the standard and control cells and for the cells to be identified;

interpreting the developed electrophoretic film by reference to a grid having a plurality of spaced lines thereon and having a sequence of symbols associated with the lines, the interpretation occurring by aligning the film with the grid by reference to the developed pattern in the track for the standard cells and determining by reference to the grid first and second symbols corresponding to the developed patterns in the tracks for the extracts from the control cells and the cells to be identified, respectively;

recording the first and second symbols so determined at first and second locations, respectively, on a data sheet;

repeating the separating, developing, interpreting and recording steps for a predetermined number of additional electrophoretically separable substances sufficient to characterize the cells to be identified, the symbols determined for these substances being recorded on the data sheet at predetermined locations located relative to the first and second locations to form a first coding sequence for the control cells and a second coding sequence for the cells to be identified;

comparing the coding sequence for the control cells with a reference coding sequence for those cells to determine whether the electrophoretic separations have been performed properly; and for properly performed separations, comparing the coding sequence for the cells to be identified with a compendium of coding sequences for known cells to determine the identity of the cells to be identified.

In accordance with a still further aspect of the invention, a method for identifying cells is provided which includes preparing a plurality of extracts from the cells to be identified, the extracts containing electrophoretically separable isoenzymes, electrophoretically separating the extracts and developing the separated extracts with regard to the isoenzymes purine nucleoside phosphorylase, glucose-6-phosphate dehydrogenase, malate dehydrogenase, mannose phosphate isomerase, peptidase B, aspartate aminotransferase and lactate dehydrogenase to produce the same insoluble product for each of the isoenzymes.

In accordance with a still further aspect of the invention, a system for identifying cells electrophoretically is provided comprising:

an extract from standard cells;

an extract from control cells;

a set of reagents for developing electrophoretic separations, each reagent being identified by a code distinct from the codes used for each other reagent, the number of reagents being chosen to permit characterization of the cells to be identified;

a set of electrophoretic films having means for receiving samples from the extracts of the standard and control cells and from an extract prepared from the cells to be identified, the films being identified by the codes used for the reagents, one code for each film; and means for interpreting the electrophoretic films including means for compiling a sequence of symbols indicative of the separation achieved for the cells to be identified for the set of reagents.

In accordance with a still further aspect of the invention, a grid is provided for use in interpreting electrophoretic separations of extracts from cells, the separation being performed on an electrophoretic film and the film having a plurality of tracks including a track for separation of an extract from standard cells and at least one track for separation of an extract from cells to be identified, which comprises a plurality of spaced lines, one of the lines serving to position the film with respect to the grid by reference to the separation in the track containing the extract from the standard cells and the remaining lines being spaced relative to the positioning line and relative to each other for discriminating differences in electrophoretic mobility between the standard cells and each of a plurality of known cells with regard to a series of preselected electrophoretically separable substances, the number of substances in the series being chosen to permit characterization of the cells to be identified.

The methods and apparatus of the invention are specifically adapted to identify cells by means of isoenzyme analysis. Among the isoenzymes for which analyses are preferably performed are purine nucleoside phosphorylase, glucose-6-phosphate dehydrogenase, malate dehydrogenase, mannose phosphate isomerase, peptidase B, aspartate aminotransferase and lactate dehydrogenase. Among the cells which preferably can be used for the standard cells are mouse L cells. Among the cells which can be used for the control cells, are HeLa cells. Among the symbols which preferably can be used to form coding sequences indicative of the various cells are letters of the alphabet. Among the ways the various reagents preferably can be identified with a distinctive code is through color-coding.

The attainment of the above objects of the invention as well as other objects is described below in connection with the description of the preferred embodiments.

BRIEF DESCRIPTION OF THE DRAWING

FIG. 3 is a plan view of a grid for use in interpreting electrophoretic separations in accordance with the invention.

FIG. 4 is a side view of the grid of FIG. 3 taken along line 4—4 in FIG. 3.

FIG. 6 also illustrates storage of electrophoretic films in a pocket which forms part of the data sheet.

FIG. 7 illustrates one page of a compendium of sequencing codes for use in identifying cells in accordance with the invention.

FIG. 8 is a plan view of an electrophoretic film supported on a plastic holder. As shown in this figure, the film lies below the holder.

FIG. 9 is a side view of the electrophoretic film and holder shown in FIG. 8.

FIG. 10 illustrates a series of seven films developed for a series of seven electrophoretically separable substances. This figure, in combination with FIGS. 1 and 6, illustrates the color coding of the reagent containers, data sheet and electrophoretic films with regard to the various reagents as indicated by the shadings and crosshatchings used on the labels on the containers, the labels on the films, and below the data entry locations on the data sheet.

FIG. 11 is a representative calibration curve for determining total enzyme activity, in this case, for the enzyme peptidase B.

DESCRIPTION OF THE PREFERRED EMBODIMENTS

Figures 1, 2:
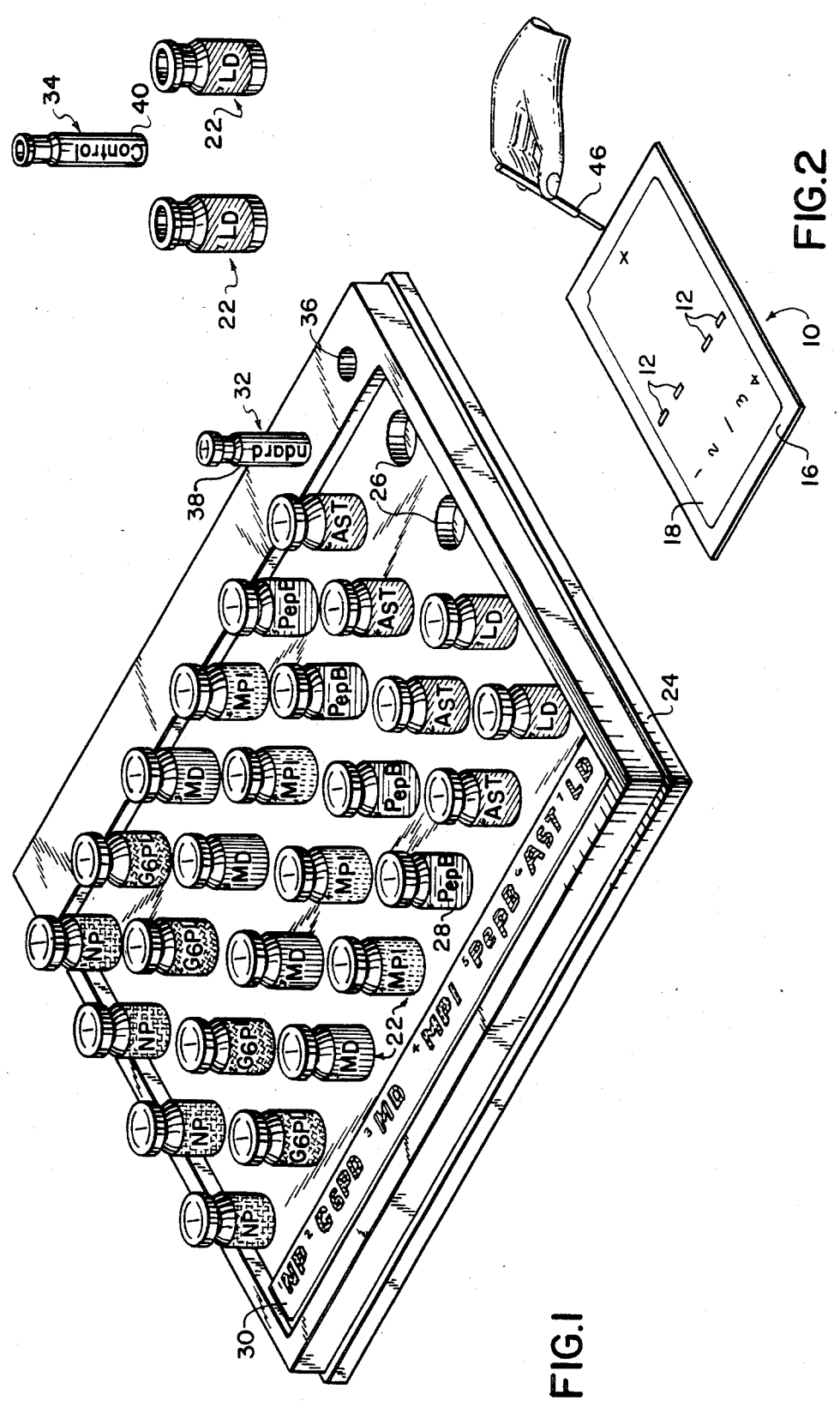
FIG. 1 is a perspective view showing the reagents and the extracts from the standard cells and the control cells as supplied to the user in accordance with a preferred embodiment of the invention.
FIG. 2 is a perspective view showing the application of a sample of a cell extract to an electrophoretic film.

The present invention provides a systematic way by which semi-skilled workers can successfully perform sophisticated electrophoretic analyses to determine the identity of cells. The user is provided with premeasured reagents for developing electrophoretic films and with standardized extracts from both standard cells and control cells. Further, he is provided with a specialized grid for interpreting electrophoretic films and a data sheet both for recording the interpretations as they are made and for compiling a sequencing code indicative of the identity of the cells to be identified. Finally, the user is supplied with a compendium of sequencing codes for previously identified cells so that a comparison can be made between the sequencing code compiled for the cells to be identified and the previously determined sequencing codes to determine the identity of the cells to be identified. By using the components of the system in the manner described below, cell identifications can be performed routinely by persons having little or no formal training in the field of electrophoretic analysis.

In the discussion that follows, specific examples of the use of the method and apparatus of the invention to perform isoenzyme analysis are given. In particular, the invention is illustrated for the seven isoenzymes—purine nucleoside phosphorylase (NP), glucose-6-phosphate (G6PD), malate dehydrogenase (MD), mannose phosphate isomerase (MPI), peptidase B (Pep B), aspartate aminotransferase (AST) and lactate dehydrogenase (LD)—and for mouse L cells as the standard cells and HeLa cells as the control cells.

It is to be understood that the invention is not limited to isoenzyme analysis, nor to the seven isoenzymes illustrated, but can be used with any electrophoretically separable substance which can be extracted from biological cells, such as proteins, and in particular, any set of isoenzymes, having more or less than seven members. Also, well-characterized cells other than mouse L and HeLa can be used as the standard and control cells, respectively. Among the cells which fall within this category are Chinese hampster ovary cells, mouse liver cells, mouse kidney cells, veal kidney cells, and the like. These cells, as well as mouse L and HeLa cells, can be used as either the control or standard cells.

The number of electrophoretically separable substances for which analyses are performed will vary with the nature of the cells to be identified. For example, if the cells to be identified are otherwise well-characterized, only a few, or even just one, electrophoretically separable substance need be analyzed. In other cases, more than the seven analyses illustrated herein may be necessary to identify the cells under study. In general, the number of substances is chosen to provide a reasonable assurance that the identification attributed to the cells to be identified is correct.

Although the invention is described in terms of analyzing extracts from populations of cells grown in tissue culture, it is to be understood that the invention is not limited to cell extracts from such sources. Rather, the invention can be used with cell extracts from any source, provided the extract contains electrophoretically separable substances. Thus, the invention can be practiced directly on cells taken from, among other things, human or animal tumors, without the need to grow the cells in tissue culture. Also, the invention can be applied to other fluids containing electrophoretically separable substances, such as blood, lymph, urine, saliva and the like, as well as to synthetic materials.

In practice, the materials needed to use the invention are preferably provided in the form of a kit or system having all of the specialized items required to identify cells in accordance with the invention. FIGS. 1–11 illustrate the components of such a kit.

FIG. 1 shows the reagent and standard and control cells extract portions of the kit. The reagents are contained in reagent containers 22. Four color-coded sets of containers 22 are provided: two sets for developing electrophoretic films and two sets for performing total enzyme analyses. Each container holds a premeasured amount of reagent for either developing an electrophoretic film or for performing a total enzyme analysis. When used for development, the premeasured reagents are dissolved in 1.0 milliliter of barbital buffer, pH 8.6; when used for total enzyme analysis, the reagents are dissolved in 5.0 milliliters of the same buffer. The buffer optionally is provided with the kit.

As shown in FIG. 1, the four reagent containers 22, for any particular reagent, are arranged in a single column in carrying tray 24. Tray 24 includes apertures 26 for receiving containers 22. It can be made of any suitable material, such as styrofoam.

In FIG. 1, for purposes of illustration, the reagent containers 22 have been arranged from left to right in the order purine nucleoside phosphorylase (NP), glucose-6-phosphate dehydrogenase (G6PD), malate dehydrogenase (MD), mannose phosphate isomerase (MPI), peptidase B (Pep B), glutamate oxalacetate transaminase, also known as aspartate aminotransferase (AST), and lactate dehydrogenase (LD). Each of the reagent containers 22 carries on its label 28 the abbreviation for the isoenzyme (e.g. NP, G6PD, MD, MPI, Pep B, AST and LD), as well as a number between 1 and 7 for the isoenzyme (e.g. 1 for NP, 2 for G6PD, 3 for MD, 4 for MPI, 5 for Pep B, 6 for AST and 7 for LD). The abbreviations and numbers also are printed on label 30, on tray 24, below each column. Further, each of the labels 28, as well as label 30 on tray 24, is colored-coded for the isoenzymes (e. g. yellow for NP, orange for G6PD, magenta for MD, purple for MPI, blue for Pep B, dark green for AST and light green for LD). The hues, tints and intensities of these colors are chosen so that even color-blind users will perceive some difference among the various labels. By use of this three tier coding approach—abbreviations, numbers and colors—the possibility that unskilled-workers will mix up the reagents is reduced to a minimum.

The four sets of reagents are provided so that one kit can be used to make two complete sets of analyses. As discussed above, each complete analysis includes electrophoretic separations and total enzyme analyses. This consumes the contents of two reagent containers 22 from each column.

Tray 24, in addition to carrying reagent containers 22, also carries containers 32 and 34 which hold extracts from two standardized cells. As discussed below, one of these extracts is used as a standard (container 32) and the other as a control (container 34). In a preferred embodiment of the invention, mouse L cells are used as the standard and HeLa cells are used as the control. Containers 32 and 34 are held in apertures 36 in tray 24; they carry "STANDARD" and "CONTROL" labels 38 and 40, respectively.

Because the reagents and extracts are heat sensitive, tray 24 and its contents preferably are stored in a refrigerator at 2°-8° C.

The standard and control extracts are supplied in freeze-dried form. Prior to use, the extracts are reconstituted in containers 32 and 34 with 200 microliters of a buffer composed of Tris (tris(hydroxymethyl)aminomethane), pH 7.5, 50% glycerine and 0.1 millimolar EDTA (ethylenediaminetetraacetic acid). Once reconstituted, the extract can be stored for extended periods of time at −20° C.

In addition to the reagents and the extracts, the kit supplied to users includes a set of electrophoretic films 10 (FIG. 2). A total of sixteen films normally are provided with each kit. Because each analysis requires seven films—one film for each of the seven isoenzymes——and because each kit has enough reagent for two complete analyses, the sixteen films are actually two more than what is needed. The two extra films are included to provide one extra film for each analysis in case a film is accidentally harmed during handling.

Electrophoretic film 10 is composed of a support 16 upon which is coated an electrophoretic medium 18 (FIG. 2). Support 16 can be made of a variety of materials including polystyrene and polyethylene terephthalate (e.g. Mylar). A preferred material is polystyrene. Electrophoretic medium 18 can consist of agar, agarose, starch, cellulose acetate, polyacrylamide, or the like, in a buffer. A preferred electrophoretic medium 18 is composed of 1% (w/v) agarose, 5% (w/v) sucrose and 0.035% (w/v) EDTA disodium salt in a 0.065M barbital buffer, p.H. 8.6. A medium of this general type is described in U.S. Pat. No. 3,766,047.

To facilitate handling of film 10, the film is supplied to the user on a plastic holder 14 (FIGS. 8 and 9). Support portion 16 of the film extends beyond holder 14 at 42 which allows the film to be peeled back and removed from the holder. Electrophoretic medium 18 is sandwiched between holder 14 and support 16 and thus is protected during shipping and handling. Holder 14 includes ports 44 which are used to apply electrophoretic medium 18 to support 16 after support 16 and holder 14 have been combined as a unit. The details of the method for applying the medium 18 to support 16, which method forms no part of the present invention, are described in U.S. Pat. Nos. 3,479,265 and 3,767,560.

Electrophoretic medium 18 includes four sample wells 12. These wells define a set of four lanes, numbered 1, 2, 3 and 4 in FIG. 8. As shown in FIG. 2, samples are applied to the medium by hand, using a micropipette 46. One sample is placed in each of wells 12. The composition of the samples applied to the individual wells is described below.

Included in the kit are a set of labels 20 for the electrophoretic films 10 (see FIG. 10). These labels carry the same three-tier coding (abbreviation, number and color) used for reagent containers 22 and label 30 on tray 24. A total of 14 labels are supplied with each kit, that is, two sets of seven labels, each of the seven being coded for a particular isoenzyme. For each complete analysis, one label 20 from each set of seven labels is applied to each of seven electrophoretic films 10 prior to removal of the films from their holders 14. This gives the user a set of seven coded electrophoretic films 10 for use in making one complete electrophoretic analysis for the seven isoenzymes for which reagents are supplied in tray 24. Labels 20 are supplied with a suitable adhesive on their front faces for attachment to the rear faces of support portions 16 of electrophoretic films 10, i.e., the faces of supports 16 which do not carry electrophoretic medium 18 (see FIG. 10).

Labels 20, in addition to being coded for the isoenzyme reagents, are provided with lane designations, specifically, the designations "standard", "control", "sample 1", and "sample 2". When labels 20 are attached to electrophoretic films 10, these designations line up with lanes 1, 2, 3 and 4, respectively, on films 10. The designations show the user which samples to place in each of sample wells 12. Thus, using micropipette 16, the user places a sample from container 32 (the standard extract container) in well 12 in lane 1, designated "standard" on label 20. Using a clean micropipette, the user then places a sample from container 34 (the control extract container) in well 12 in lane 2, designated "control" on label 20. Finally, again using clean micropipettes, the user places a sample from each of up to two cell extracts to be identified in the sample wells 12 of lanes 3 and 4, corresponding to the designations "sample 1" and "sample 2". One microliter samples can be used. This process is repeated for each of the seven electrophoretic films 10 to which a label 20 has been applied. Note that a total of four cell populations can be analyzed with one kit; each kit includes enough suplies for two complete analyses, and each analysis can accept samples from two cells to be identified. The two sets of reagents for use in determining total enzyme activity similarly are sufficient to perform two analyses each for each set.

In addition to the reagents and the films, the kit also includes a grid 48 for interpreting electrophoretic films 10 (FIGS. 3 and 4). Grid 48 includes body 50 and alignment bumper 52 which projects above body 50 at the left-hand side of grid 48. Body 50 carries thereon a plurality of spaced lines 54 having associated therewith letters of the alphabet 56. Body 50 also includes a thick line 58 which is designated "STANDARD".

As is discussed in detail below, after samples have been placed in sample wells 12 for the complete series of seven electrophoretic films 10, the films are subjected to electrophoretic separation on electrophoretic separation apparatus. Next, they are developed with the reagents contained in reagent containers 22, one reagent being used for each film, wih the three tier coding on film labels 20 and reagent labels 28 being used to select the appropriate reagent for each film. This process causes colored bands 60 to appear in the lanes of electrophoretic film 10. Normally, the reagents and the standard and control cells are chosen so that at least one band occurs in each of lanes 1 and 2. Whether bands appear in lanes 3 and 4 for samples 1 and 2 depends on the characteristics of the cells to be identified, although normally the analysis is structured so that most cells produce a band. The locations of the bands in lanes 3 and 4 are indictative of the cells to be identified. Grid 48 is used as the first step in interpreting these locations so as to arrive ultimately at an identification of the cells to be identified.

Figure 5:
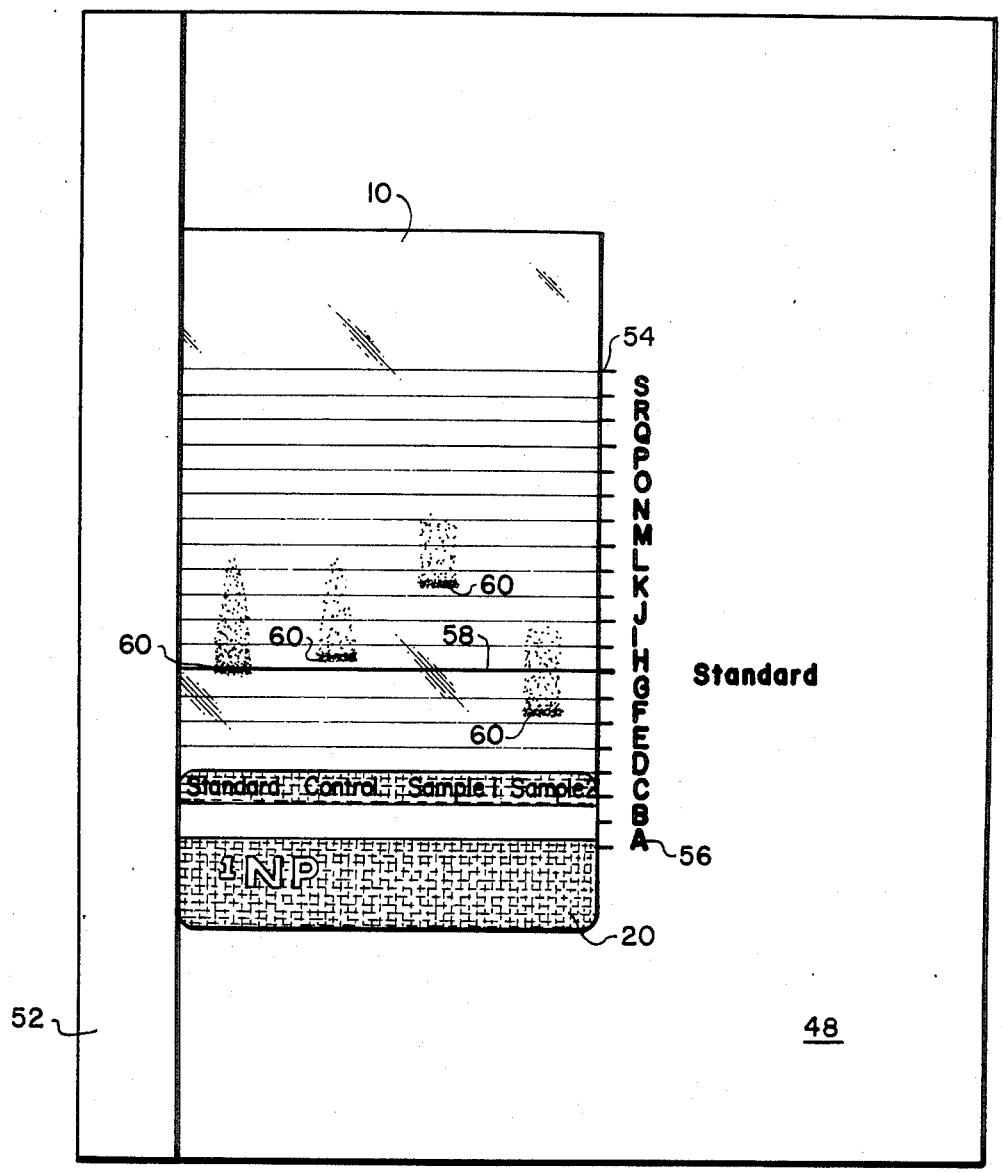
FIG. 5 is a plan view of the grid of FIG. 3 with an electrophoretic film in place for interpretation.

The use of grid 48 is illustrated in FIG. 5. As shown therein, an electrophoretic film 10 is aligned with the grid 48 in two ways—first, by sliding the film against alignment bumper 52, and second, by placing band 60 in the lane designated "standard" over thick line 58, i.e., the "standard" line. Once this alignment has been made, the user reads off a letter of the alphabet 56 (or letters of the alphabet, if appropriate), corresponding to the location of band 60 in each of the lanes designated "control", "sample 1" and "sample 2". For example, in FIG. 5, the letters for these three lanes are H, K and F, respectively. It should be noted that although letters of the alphabet 56 have been used in FIGS. 3 and 5, other symbolic representations, e.g., numbers, could be used equally as well.

FIG. 5 shows grid 48 being used for an electrophoretic film 10 carrying a label 20 designating purine nucleoside phosphorylase, NP. The same interpretation process is carried out for each of the other films in the series. That is, each film is aligned with bumper 52 and thick line 58, and a letter (or letters) of the alphabet 56 is assigned to the location of the bands in the "control" lane and to the bands, if present, in the "sample 1" and "sample 2" lanes. Accordingly, when the process has been completed for all seven films, the user will have, in the usual case, three series of seven letters, one series for each of the control, sample 1 and sample 2. To keep track of this data and the steps of the interpretation, the kit includes data sheet 62 (FIG. 6).

Figure 6:
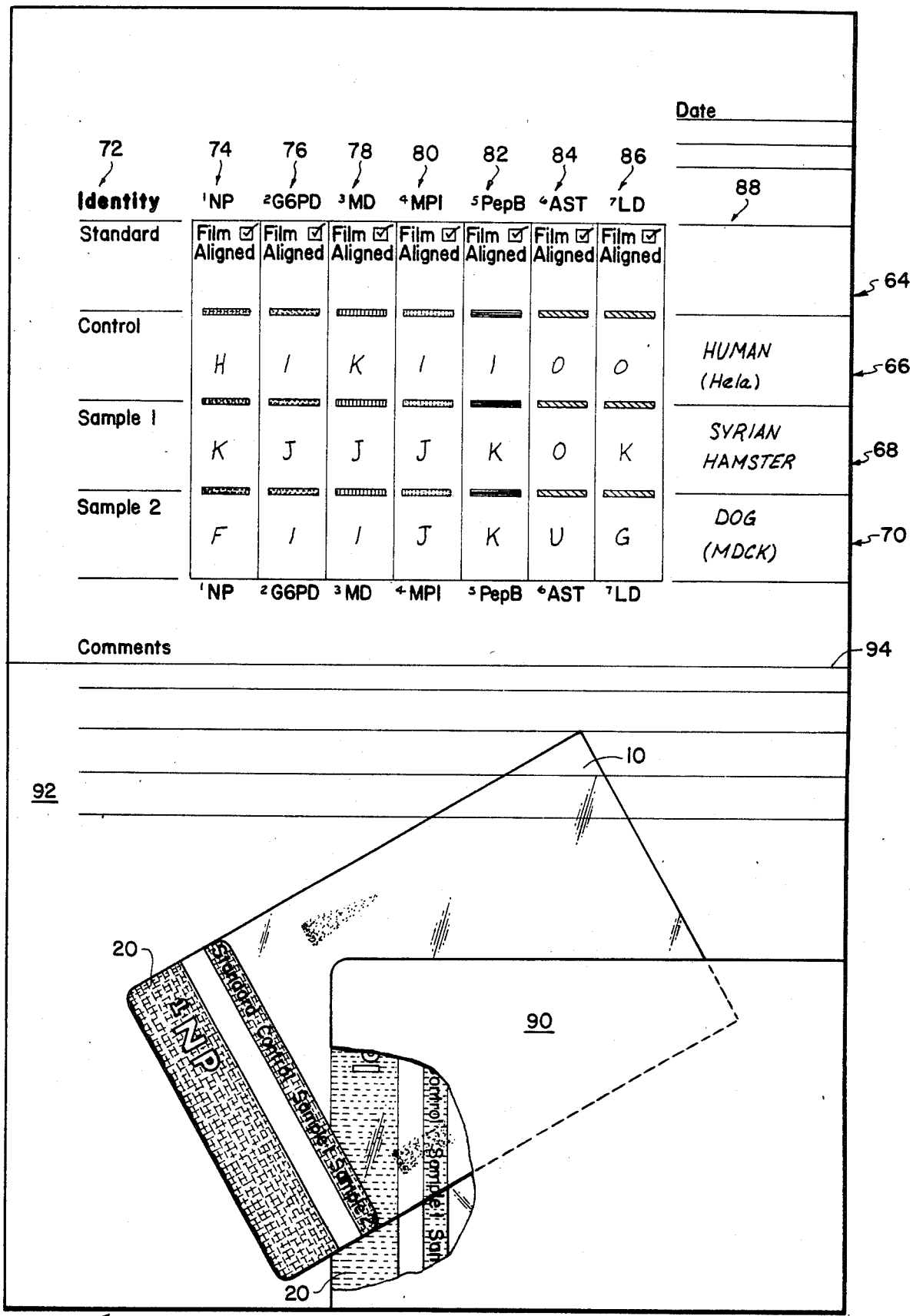
FIG. 6 is a plan view of a data sheet for use in compiling sequencing codes to identify cells in accordance with the invention.

Data sheet 62, in the embodiment shown in FIG. 6, includes four rows 64, 66, 68 and 70 and nine columns 72, 74, 76, 78, 80, 82, 84, 86 and 88. It also includes pocket 90 for holding developed electrophoretic films 10 and a portion 92 for recording comments. The data sheet is designed to fold about line 94 to provide a convenient package for storing cell identification information.

The four rows 64, 66, 68 and 70 of data sheet 62 correspond to the "standard", "control", sample 1" and "sample 2" lanes of electrophoretic films 10. Columns 74 through 86 correspond to the seven isoenzymes for which electrophoretic films 10 have been developed. These columns carry the same three tier coding—abbreviations, numbers and colors—as used to code film labels 20 and reagent container labels 28. Column 72 identifies rows 64, 66, 68 and 70 as relating to the "standard", "control", "sample 1" and "sample 2". Column 88 is used to record the ultimate identification of the cells to be identified, the process for which is described below.

Data sheet 62 is used in conjunction with grid 48 by recording in the appropriate column and row the letters 56 determined for each lane of each electrophoretic film 10. Thus, for example, for the NP film shown in FIG. 5, an H is recorded in column 74, row 66, corresponding to the band at level H in the "control" lane (lane number 2) of electrophoretic film 10. Similarly, for lane 3, a K is recorded in column 74, row 68, and for lane 4, an F is recorded in column 74, row 70. All the recordings are made in column 74, because this column corresponds to the NP electrophoretic film shown in FIG. 5. The three tier coding serves to minimize transposing data for the seven isoenzymes. Row 64 of data sheet 62 includes a check-off box entitled "film aligned" to serve as a reminder that the letters 56 are to be read only after the film has been aligned with bumper 52 and thick line 58.

The process used for the NP electrophoretic film 10 is repeated for the remaining six electrophoretic films in the series, each letter 56 being entered in its appropriate space under the guidance of the three tier code and the cell identifications in column 72. Upon completion of these steps, which can be performed by persons with very little experience in electrophoretic analysis, there will exist on data sheet 62 a compiled coding sequence of letters 56 corresponding to the control cells (row 66), the sample 1 cells (row 68) and the sample 2 cells (row 70). For example, in FIG. 6, the coding sequence for the control is HIKIIOO, for sample one, KJJJKOK and for sample 2, FIIJKUG. With these coding sequences in hand, the final step of the identification is performed: comparing the compiled coding sequences with known coding sequences to determine the identity of the cells to be identified. This is done by means of a compendium of coding sequences. FIG. 7 illustrates a page, identified by the number 96, of such a compendium prepared in printed book form.

The compendium is compiled by conducting electrophoretic separations on numerous known cells and interpreting those separations using grid 48 and data sheet 62 to compile a sequencing code for each of the known cells. The separations are run under the conditions to be used in identifying cells to be identified. A detailed discussion of these conditions is presented below in connection with the description of how extracts are prepared and electrophoretic separations are performed. Briefly, one set of variables which preferably are kept constant are the sizes, types and thicknesses of the electrophoretic media 18 of electrophoretic films 10. Other variables include the time, field strength and temperatures at which the electrophoretic separations are performed.

As explained below, greater variability can be tolerated in the separation and development conditions because the pattern for the cells to be identified is compared with the pattern for the standard cells. Since these two patterns are created and developed on the same electrophoretic film 10, discrepancies from the prescribed conditions tend to effect both patterns more or less equally, so that the differences between the patterns, which is what is measured to determine the identity of the cells to be identified, remains generally constant. And, as also explained below, by using an extract of control cells, again on the same electrophoretic film 10, a ready check is provided to determine if the limits of variability have been exceeded.

Once the sequencing codes for various known cells have been determined, the codes are arranged in the compendium in any convenient order. The compendium can be in the form of a printed book as illustrated in FIG. 7 or can be in the form of a data base for a computer, microprocessor, or the like. These latter forms for the compendium are preferable for analyses based on large numbers of isoenzymes, e.g. forty or fifty isoenzymes, rather than seven as used for illustration herein, and for large compilations of sequencing codes for known cells.

After the initial round of sequencing code determinations for known cells has been made and placed in the compendium, additional entries can be made as more known cells are studied and their sequencing codes determined. The compendium, whether in book form or otherwise, can be supplied with each kit or as a separate item. Updated editions of the compendium also can be issued as sequencing codes for more cells are determined.

Using the compendium, the ultimate identification of the cells to be identified is made and entered into column 88 of data sheet 62. This is done by first comparing the sequencing code for the control cells (row 66) with the compendium. If the electrophoretic separations and development have been done properly, the sequencing code for the control should agreee with the sequencing code given in the compendium for the control cells. Thus, for our illustrative example of HeLa control cells, the coding sequence which appears in row 66 should be the same as the sequence which appears in the compendium for HeLa cells. This is an important check on the operation of the system and is one of the aspects of the invention that allows sophisticated electrophoretic analyses to be performed by semi-skilled workers. By receiving feedback in the form of a match between the sequencing code determined for the control cells and the known sequencing code for those cells, the worker knows that he has performed the analysis properly. This gives the worker confidence in his results, and allows others to rely on his work. Also, if a match is not achieved, the worker immediately knows that the compendium should not be used in interpreting the coding sequences for samples 1 and 2 (rows 68 and 70 respectively). Other techniques of interpretation, discussed below, may then be appropriate.

Assuming there is a match between the sequencing code in row 66 for the control cells and the known sequencing code for those cells, the worker then consults the compendium for sequencing codes corresponding to the sequencing codes compiled for samples 1 and 2 (rows 68 and 70 respectively). If matches are found, the cell identifications associated with the codes in the compendium are entered in column 88 of data sheet 62, thus completing the analysis. For example, in FIG. 6, the sample 1 and sample 2 sequencing codes correspond to the sequencing codes for Syrian hampster and dog in FIG. 7. If the coding sequence is not found, it may be appropriate to report the new coding sequence to the compiler of the compendium and to investigate the possibility of identifying the cells to be identified by non-electrophoretic methods so as to be able to update the compendium with an additional sequencing code.

As described above, grid 48 includes a series of spaced lines 54 having associated therewith symbols 56 which make up the sequencing codes used to identify cells. Although the lines are shown equally spaced in FIGS. 3 and 5, it is to be understood that the lines do not have to be so spaced. Also, other forms of grids, such as linear or circular sliding grids can be used, provided they result in assigning a symbolic representation to the relative spacing between electrophoretically separated and developed bands of standard cells and other types of cells.

In general terms, the specific grid 48 shown in FIGS. 3 and 5 and other types of grids are designed in view of the series of electrophoretically separable substances subject to analysis, the conditions used for the electrophoretic separations, and the nature of the standard cells which are used. That is, the grid is chosen so that by aligning the grid based on the band produced for the standard cells, symbolic representations can be assigned to numerous cells to be identified for a series of preselected substances. For the seven isoenzymes used for illustration herein, mouse L cells as the standard, and the electrophoretic separation equipment and conditions described below, it has been found that a grid of twenty equally spaced lines, 4 millimeters apart, can be used to assign symbolic representations to the electrophoretic bands observed for the seven isoenzymes for a plurality of cells presently grown in tissue culture including rat, hamster, rabbit, mink, monkey, cow, dog, marmoset, gibbon and chimpanzee cells. For other isoenzymes, standard cells, or electrophoretic equipment or procedures, similar grids can be developed.

As mentioned above, it may happen that the coding sequence compiled for the control cells is not in agreement with the known coding sequence for those cells. In such a case, the separation data may still be salvageable. For example, the coding sequences may be different with respect to only one isoenzyme, and the coding sequences for the unknown samples 1 and 2 may be interpretable, with reasonable confidence, without reference to that isoenzyme. Alternatively, a correction may be made to the symbols assigned to the cells to be identified for the errant isoenzyme, based on the difference between what the symbol for the control cells should have been and what was actually observed.

In practice, the kit is used in the following manner. First, two cell extracts are prepared which contain electrophoretically separable substances from the cells to be identified (sample 1 and sample 2). The extracts can be prepared in a number of ways known to the art. One such way involves disrupting the cells by freezing and centrifuging the disrupted cells to produce the desired extract in the form of the supernatant liquid which contains electrophoretically separable substances.

Once the extracts have been prepared, samples from each extract are introduced into sample wells 12 in lanes 3 and 4, respectively, of seven electrophoretic films 10. Samples from the standard and control extracts supplied with the kit are introduced into lanes 1 and 2, respectively, of each film. The seven electrophoretic films 10 have previously had applied thereto labels 20, as described above.

Once all the samples have been deposited in the sample wells 12 of the series of electrophoretic films 10, each film is subjected to electrophoretic separation. The electrophoretic separation can be accomplished with standard electrophoretic separation apparatus known in the art. In the case of isoenzyme analysis, the electrophoretic separation apparatus should include means for preventing an increase in the temperature of electrophoretic film 10 during the electrophoretic separation process so as to avoid the inactivation of the isoenzymes. In particular, for the seven isoenzymes used illustratively herein, it has been found that the temperature of the film should be maintained between 4° C. and 10° C. throughout the separation. One especially convenient electrophoretic separation apparatus for performing the separation and maintaining the temperature of the film within the preferred range is described in copending and commonly assigned U.S. patent application Ser. No. 416,462, now abandoned.

Using the electrophoretic apparatus described in the above-referenced application, it was determined that satisfactory separations could be achieved for the seven isoenzymes for a variety of cell types using thin film agarose electrophoretic films having a polystyrene support and composed of 1% (w/v) agarose, 5% (w/v) sucrose and 0.035% (w/v) EDTA disodium salt in a 0.065M barbital buffer, p.H. 8.6 (Corning Medical Catalog #470100); an electrode buffer of barbital, pH 8.6; 500 milliliters of tap water, 4° C. to 8° C., as the cooling medium in the separation apparatus; an applied field strength of 27 V/cm achieved by placing a steady 160 volts across the electrodes of the separation apparatus; and conducting the separation for 25 minutes.

Moreover, by performing the separations in this manner, it was found that the developed bands for all of the isoenzymes and for a large variety of cells could be interpreted using the linear grid shown in FIGS. 3 and 5, with a spacing of 4 millimeters between lines and a total of twenty lines, and with mouse L cells used as the standard. Among the species which were found interpretable with grid 48 under the above conditions were rat, hamster, rabbit, mink, monkey, cow, dog, marmoset, gibbon and chimpanzee.

Once the electrophoretic separation has proceeded for the prescribed period of time, the apparatus is shut off and the electrophoretic films 10 removed. Reagent from one set of reagent containers 22 is then dissolved in barbital buffer, as described above, and spread evenly over electrophoretic media 18, one reagent container being used for each film 10, the reagent containers and the films being matched by means of the three tier coding system described above. Excess reagent is rolled off each electrophoretic film 10 with a pipette or stirring rod used sideways. Films 10 are then placed in a moist chamber at 37° C. and incubated for 20 minutes in the dark. Next, the films are removed and washed twice in deionized water at 10 minute intervals. In the case of agarose based films, the washing step is followed by air drying at approximately 60° C. which causes the agarose to collapse onto and bond with the support portion 16 of electrophoretic films 10. This completes the separation and developing processes for electrophoretic films 10, after which the films are interpreted as described above using grid 48, data sheet 62 and the compendium of sequencing codes for known cells.

Reagents which have been found preferable for developing the seven isoenzymes used herein to illustrate the invention have the following compositions:

| Purine nucleoside phosphorylase: | |
|---|---|
| inosine, | 13.41 mg |
| xanthine oxidase, | 1 unit |
| MTT, | 7.0 mg |
| PMS, | 0.06 mg |
| EDTANa$_2$ | 0.186 mg |
| sodium salicylate, | 0.08 mg |
| KH$_2$PO$_4$ | 49.98 mg |
| K$_2$HPO$_4$ | 30.21 mg |
| Glucose-6-phosphate dehydrogenase: | |
| NADP | 1.97 mg |
| MgCl$_2$ | 6.1 mg |
| G-6-PNa | 7.1 mg |
| MTT | 5.0 mg |
| PMS | 0.06 mg |
| oxidized glutathione | 3.15 mg |
| Malate dehydrogenase: | |
| NAD | 19.9 mg |
| sodium malate | 31.2 mg |
| MTT | 5.0 mg |
| PMS | 0.06 mg |
| EDTANa$_2$ | 0.005 mg |
| oxidized glutathione | 3.15 mg |
| Mannose phosphate isomerase: | |
| mannose-6-phosphate | 15.2 mg |
| glucose phosphate isomerase | 20 units |
| glucose-6-phosphate dehydrogenase | 20 units |
| NAD | 6.63 mg |
| MgCl$_2$.6H$_2$O | 6.1 mg |
| MTT | 5.0 mg |
| PMS | 0.06 mg |
| citrate buffer | 1.42 mg |
| ovalbumin | 1.0 mg |
| oxidized glutathione | 3.15 mg |
| Peptidase B: | |
| L-Leuglygly | 30.66 mg |
| L-amino acid oxidase | 0.1 unit |
| MTT | 5.17 mg |
| PMS | 0.06 mg |
| manganese Cl$_2$ | 4.94 mg |
| mannitol | 50.00 mg |
| Aspartate aminotransferase: | |
| L-aspartic acid | 7.75 mg |
| 2-oxoglutaric acid | 1.46 mg |
| NAD | 13.26 mg |
| glutamic acid dehydrogenase | 50 units |
| MTT | 5.0 mg |
| diaphorase | 20 units |
| pyridoxal-5-phosphate | 0.1 mg |
| adenosine diphosphate | 4.62 mg |
| flavine mononucleotide | 0.05 mg |
| Lactate dehydrogenase: | |
| L-lithium lactate | 14.4 mg |
| NAD | 19.9 mg |

| | |
|---|---|
| -continued | |
| MTT | 5.0 mg |
| PMS | 0.06 mg |
| oxidized glutathione | 3.15 mg | where NAD is nicotinamide adenine dinucleotide, NADP is nicotinamide adenine dinucleotide phosphate; PMS is phenazine methosulfate; MTT is 3-(4,5-dimethyl-2-thiazolyl)-2,5-diphenyl-2H-tetrazolium-bromide. The components for the Peptidase B reagent are directly placed into reagent containers 22. The components of the remaining reagents are combined with 1 milliliter water, freezed dried and the resulting powder placed in containers 22. Prior to freeze drying, the pH of these reagents is adjusted with HCl to the following values: NP-pH 6.2; G6PD-pH 2.0; MD-pH 4.0; MPI-pH 6.0; AST-pH 6.0; LD-pH 4.0. To use the dry reagents, the user adds either 1 or 5 milliliters of barbital buffer, pH 8.6, depending on whether an electrophoretic or total enzyme analysis is to be performed, respectively.

Each of these reagents uses the transformation of a soluble tetrazolium dye to an insoluble formazan to localize its respective isoenzyme. Each formazan used is colored either purple-blue or purple-red. Accordingly, all of the films, as well as all of the total isoenzyme analyses, will have similar colors. This is of benefit in making the system easy to use by semi-skilled workers because it tends to give a sense of uniformity to the overall process. Tetrazoliums producing other colors, such as yellows or reds, can also be used, as well as other insoluble read-out materials having a single family of colors for the various reagents.

As discussed above, four sets of reagent containers 22 are included in each kit: two for conducting electrophoretic separations and two for total enzyme activity determinations. Total enzyme activity is determined using these reagents by dissolving the dry reagents in 5 milliliters of barbital buffer and reacting 100 microliters of the dissolved reagents with 10 microliter samples of the extracts from the cells to be identified. The reaction is allowed to proceed for 10 minutes after which it is stopped by adding 1 ml of a stopping reagent (0.05M HCl+1% Triton X-100 in deionized water). The absorbance of the reaction mixture is then read against a reagent blank on a spectrophotometer set at 565 nm. The optical density so measured is then converted to activity units using a calibration curve. On such calibration curve for peptidase B is shown in FIG. 11. This curve was obtained using 10 microliter samples of the reagent for peptidase B, amounts of L-leucine varying from 10 to 400 nanomoles and 1.0 ml of the stopping reagent. The changes in optical density at 565 nm were measured against reagent blanks for the various amounts of L-leucine, and the curve shown in FIG. 11 was derived by defining one activity unit as the amount of peptidase B which forms one micromole of L-leucine/minute at 37° C. Similar curves are obtained in the same manner for the other reagents using varying amounts of the product produced by the reaction of the isoenzyme with its reagent.

The results of the electrophoretic separations on electrophoretic films 10 and the total isoenzyme analyses can be combined to determine the activity represented by any particular band of patterns having more than one band. Using a spectrophotometer, the optical density of each band in a pattern can be determined as well as the total optical density for all the bands. From this information, the percentage optical densities of each band can be calculated, which when multiplied by the total isoenzyme activity, gives the activity represented by each band.

As discussed above, the preferred standard and control cells are mouse L cells and HeLa cells, respectively. Extracts of these cells for incorporation in the kit can be prepared by centrifuging, washing and suspending the cells in a buffer composed of 50 mM Tris, pH 7.5, 1 mM EDTA and 1.0% Triton X-100, disrupting the cells by forcefully expressing them through a pasteur pipet three times, centrifuging the crude extract and removing the supernatant liquid. The supernatant liquid is then placed in containers 32 or 34 as appropriate and freeze-dried in the containers.

Althrough specific embodiments of the invention have been described and illustrated, it is to be understood that modifications can be made without departing from the invention's spirit and scope. Thus, although the invention has been illustrated with reference to isoenzyme analysis, it is equally applicable to all types of electrophoretically separable substances. Similarly, although the sequencing code has been illustrated using letters of the alphabet as the symbols, other symbols can be used. In the sane vein, other grids, data sheets, and reagent coding systems can be substituted for those illustrated.

What is claimed is:

1. An electrophoretic method for identifying cells comprising the steps of:
    (a) simultaneously performing on an electrophoretic film, multiple electrophoretic separations on a sample from a control, a standard population of cells, and at least one sample from an unknown population of cells each of the samples containing a least some electrophoretically separable substances which are characteristic of all the cells;
    (b) developing the electrophoretic separations of control, standard, and unknown cells with regard to an electrophoretically separable, characteristic substance;
    (c) comparing the developed separations for the control and standard samples to determine the range of separation for the characteristic substance under the conditions used; and
    (d) based on the range of separation so determined, comparing the separations for the unknown and standard samples to identify the unknown cells.

2. The method of claim 1 wherein the electrophoretically separable substances are proteins.

3. The method of claim 2 wherein the electrophoretically separable substances are isoenzymes.

4. The method of claim 3 wherein the isoenzymes are purine nucleoside phosphorylase, glucose-6-phosphate dehydrogenase, malate dehydrogenase, mannose phosphate isomerase, peptidase B, aspartate aminotransferase and lactate dehydrogenase.

5. The method of claims 1, 2, 3 or 4 wherein the control population of cells is a population of mouse L cells.

6. The method of claim 5 wherein the standard population of cells is a population of HeLa cells.

7. The electrophoretic method of claim 1 comprising:
    (a) performing electrophoretic separations on a series of samples from the unknown population of cells;
    (b) developing the electrophoretic separations of the unknown samples with regard to a series of different, preselected characteristic substances;

(c) determining from the developed samples the electrophoretic mobility exhibited by the unknown cells to be identified for each of the preselected substances;

(d) assigning to the electrophoretic mobility for each substance so determined a symbolic representation;

(e) arranging the symbolic representations in a predetermined order to form a coding sequence for the unknown population of cells; and (f) comparing the coding sequence of the unknown population of cells with a compendium of predetermined coding sequences for known cells to identify the unknown cells.

8. The method of claim 7 wherein the electrophoretic mobility is determined using a grid having a plurality of spaced lines by which the symbolic representations are assigned.

9. The method of claims 7 or 8 wherein the symbolic representations are letters of the alphabet.

10. The method of claims 7 or 8 wherein the electrophoretically separable substances are proteins.

11. The method of claims 7 or 8 wherein the electrophoretically separable substances are isoenzymes.

12. The method of claims 7 or 8 wherein the series of electrophoretically separable substances consists of purine nucleoside phosphorylase, glucose-6-phosphate dehydrogenase, malate dehydrogenase, mannose phosphate isomerase, peptidase B, aspartate aminotransferase and lactate dehydrogenase.

13. The method of claims 7 or 8 wherein the electrophoretically separable substances are developed to produce a group of similar colors.

14. The method of claim 13 wherein the electrophoretically separable substances are developed to form an insoluble formazan which is colored purple-blue or purple-red.

15. A method for identifying cells comprising the steps of:

(a) electrophoretically separating extracts from standard cells, control cells and the unknown cells to be identified simultaneously on separate tracks of an electrophoretic film;

(b) developing the electrophoretic film with regard to a first preselected electrophoretically separable characteristic substance using a reagent specific for that substance to produce a pattern of one or more bands of an insoluble product in each track for which the substance is present in the extract, the pattern, where present, being indicative of the extent of electrophoretic migration of the first preselected substance for the standard, control, and unknown cells;

(c) interpreting the developed electrophoretic film by reference to a grid having a plurality of spaced lines thereon and having a sequence of symbols associated with the lines, the interpretation occurring by aligning the film with the grid by reference to the developed pattern in the track for the standard cells and determining by reference to the grid first and second symbols corresponding to the developed patterns in the tracks for the extracts from the control cells and the unknown cells, respectively;

(d) recording the first and second symbols so determined at first and second locations, respectively, on a data sheet;

(e) repeating steps a, b, c, and d for a predetermined number of additional electrophoretically separable characteristic substances, the symbols determined for these substances being recorded on the data sheet at predetermined locations located relative to the first and second locations to form a first coding sequence for the control cells and a second coding sequence for the unknown cells;

(f) comparing the coding sequence for the the control cells with a reference coding sequence for those cells to determine whether the electrophoretic separations have been performed properly; and (g) for properly performed separations, comparing the coding sequence for the unknown cells with a compendium of predetermined coding sequences for known cells to identify the unknown cells.

16. The method of claim 15 wherein the electrophoretically separable substances are proteins.

17. The method of claim 15 wherein the electrophoretically separable substances are isoenzymes.

18. The method of claim 17 including the additional step of determining the total isoenzyme activity of the cells to be identified for one or more of the isoenzymes for which an electrophoretic separation has been developed.

19. The method of claim 18 including the additional step of determining the isoenzyme activity represented by each band of a developed pattern having more than one band by apportioning the total isoenzyme activity among the bands based on the relative optical densities of the bands.

20. The method of claim 15 wherein the electrophoretic films, the reagents and the data sheet are color-coded with respect to the electrophoretically separable substances, one color being used to identify each substance.

21. The method of claim 15 wherein the symbols are letters of the alphabet.

22. The method of claims 17, 18 or 19 wherein the isoenzymes are purine nucleoside phosphorylase, gluocose-6-phosphate dehydrogenase, malate dehydrogenase, mannose phosphate isomerase, peptidase B, aspartate aminotransferase and lactate dehydrogenase.

23. The method of claims 15, 16, 17, 18 or 19 wherein the same insoluble product is produced during development for each of the electrophoretically separable substances.

24. The method of claim 23 wherein the insoluble product is a formazan.

25. A system for identifying cells electrophoretically comprising:

(a) extracts from a standard and a control cells;

(b) an extract from an unknown cells;

(c) a set of reagents for developing characteristic substances in electrophoretic separations of the standard, control, and unknown cells, each reagent being identified by a code distinct from the codes used for each other reagent, the number of reagents being chosen to permit characterization of the unknown cells;

(d) a set of electrophoretic films having means for receiving samples from the extracts of the standard, control, and unknown cells, the films being identified by the codes used for the reagents, one code for each film;

(e) an electrophoretic device; and (f) means for interpreting the electrophoretic films including means for compiling a sequence of symbols indicative of the separation achieved for the developed characteristic substances of the unknown cells.

26. The system of claim 25 wherein the symbols are associated with a grid of spaced lines.

27. The system of claim 25 wherein the compiling means is coded with the codes for the reagents.

28. The system of claim 25 wherein the reagents develop the electrophoretic separations for the presence of proteins.

29. The system of claim 25 wherein the reagents develop the electrophoretic separations for the presence of isoenzymes.

30. The system of claim 29 further including a second set of reagents identified by the same code as the first set of reagents for determining total isoenzyme activity of the cells to be identified.

31. The system of claims 25, 28, 29 or 30 wherein the reagents are premeasured.

32. The system of claims 29 and 30 wherein the isoenzymes are purine nucleoside phosphorylase, glucose-6-phosphate dehydrogenase, malate dehydrogenase, mannose phosphate isomerase, peptidase B, aspartate aminotransferase and lactate dehydrogenase.

33. The system of claims 25, 28, 29 or 30 wherein the reagents develop the electrophoretic separations to a group of similar colors.

34. The system of claim 32 wherein each of the reagents includes a soluble tetrazolium dye which is reduced to an insoluble formazan which is colored purple-blue or purple-red.

35. The system of claims 25, 28, 29 or 30 wherein the standard cells are mouse L cells and the control cells are HeLa cells.

36. The system of claim 25 further including means for decoding the sequence of symbols to determine the identity of the cells to be identified.

37. The system of claim 36 wherein the decoding means is a compendium of known sequences of symbols for known cells.

38. The system of claims 25, 29 or 30 wherein the code is a color code.

* * * * *